US012642758B2

(12) United States Patent
Sahin et al.

(10) Patent No.: US 12,642,758 B2
(45) Date of Patent: Jun. 2, 2026

(54) USE OF PLANT EXOSOMES FOR ENHANCING VIABILITY AND HAIR GROWTH CAPACITY OF SKIN CELLS

(71) Applicant: YEDITEPE UNIVERSITESI, Istanbul (TR)

(72) Inventors: Fikrettin Sahin, Istanbul (TR); Pakize Neslihan Tasli, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 942 days.

(21) Appl. No.: 17/639,614

(22) PCT Filed: Sep. 2, 2020

(86) PCT No.: PCT/TR2020/050796
§ 371 (c)(1),
(2) Date: Mar. 2, 2022

(87) PCT Pub. No.: WO2021/045712
PCT Pub. Date: Mar. 11, 2021

(65) Prior Publication Data
US 2022/0331230 A1      Oct. 20, 2022

(30) Foreign Application Priority Data
Sep. 2, 2019      (TR) ................................. 2019/13215

(51) Int. Cl.
| | |
|---|---|
| *A61K 8/9789* | (2017.01) |
| *A61K 8/14* | (2006.01) |
| *A61K 8/9794* | (2017.01) |
| *A61K 36/185* | (2006.01) |
| *A61K 36/88* | (2006.01) |
| *A61K 36/8962* | (2006.01) |
| *A61P 17/14* | (2006.01) |
| *A61Q 7/00* | (2006.01) |
| *A61Q 19/08* | (2006.01) |

(52) U.S. Cl.
CPC .......... *A61K 8/9789* (2017.08); *A61K 36/185* (2013.01); *A61K 36/88* (2013.01); *A61K 36/8962* (2013.01); *A61P 17/14* (2018.01); *A61Q 7/00* (2013.01)

(58) Field of Classification Search
None
See application file for complete search history.

(56) References Cited

U.S. PATENT DOCUMENTS

| | | | | |
|---|---|---|---|---|
| 6,630,163 | B1 * | 10/2003 | Murad .................... | A61K 36/87 424/59 |
| 10,881,706 | B2 * | 1/2021 | Sahin .................... | A61K 36/899 |
| 11,130,005 | B2 * | 9/2021 | Lee .......................... | A61K 8/14 |
| 11,690,797 | B2 * | 7/2023 | Yi .......................... | A61K 8/044 424/401 |

| | | | |
|---|---|---|---|
| 2013/0209528 | A1 | 8/2013 | Levi et al. |
| 2013/0216596 | A1 | 8/2013 | Viladot Petit et al. |
| 2018/0256488 | A1 * | 9/2018 | Choi .................... A61K 8/9789 |
| 2018/0271773 | A1 * | 9/2018 | Lee .......................... A61P 17/00 |
| 2018/0275029 | A1 * | 9/2018 | Yamawaki ........... G01N 1/4055 |

FOREIGN PATENT DOCUMENTS

| | | | |
|---|---|---|---|
| CN | 106974221 A | 7/2017 | |
| EP | 2629782 A1 | 8/2013 | |
| EP | 3354257 A1 | 8/2018 | |
| KR | 20140126973 A | 11/2014 | |
| WO | 2017023690 A1 | 2/2017 | |
| WO | WO-2017052271 A1 * | 3/2017 | ........... A61K 31/522 |
| WO | 2017057881 A1 | 4/2017 | |
| WO | 2017078641 A1 | 5/2017 | |

OTHER PUBLICATIONS

Perez-Bermudez et al., Extracellular vesicles in food: Experimental evidence of their secretion in grape fruits. 98: 40-50. (Year: 2017).*
Kim, Jongmin, et al. "Isolation of high-purity extracellular vesicles by extracting proteins using aqueous two-phase system." PloS one 10.6 (2015): e0129760. (Year: 2015).*
Shin, Hyunwoo, et al. "High-yield isolation of extracellular vesicles using aqueous two-phase system." Scientific reports 5.1 (2015): 13103. (Year: 2015).*
Allison Beach, et al., Exosomes: an overview of biogenesis, composition and role in ovarian cancer, Journal of Ovarian Research, 2014, pp. 1-10, vol. 7, No. 14.
Anna-Kristin Ludwig, et al., Exosomes: Small vesicles participating in intercellular communication, The International Journal of Biochemistry & Cell Biology, 2012, pp. 11-15, vol. 44.
Nunzio Iraci, et al., Focus on Extracellular Vesicles: Physiological Role and Signalling Properties of Extracellular Membrane Vesicles, International Journal of Molecular Sciences, 2016, pp. 1-32, vol. 17, No. 171.
B. Stegmayr, et al., Promotive Effect on Human Sperm Progressive Motility by Prostasomes, Urological Research, 1982, pp. 253-257, vol. 10.
Otar T. Norwood, Male Pattern Baldness: Classification and Incidence, Southern Medical Journal, 1975, pp. 1359-1365, vol. 68, No. 11.

(Continued)

*Primary Examiner* — Bethany P Barham
*Assistant Examiner* — Peter Anthopolos
(74) *Attorney, Agent, or Firm* — Bayramoglu Law Offices LLC

(57)      ABSTRACT

A use of plant exosomes as a product having the effect of enhancing viability and, by stimulating the hair follicles, enhancing hair growth in skin cells. The plant exosomes are used to revitalize and strengthen unhealthy skin and hair that have lost their vitality, to stop hair loss, to provide faster hair growth by stimulating hair follicles, and to provide a regulating effect in improving the effects such as wrinkles and age spots caused by aging skin cells. The plant exosomes are isolated from single, double, or triple combinations of plants selected from a group consisting of pineapple plant, garlic plant, and pomegranate plant. For example, a triple combination includes 1 ng-1 mg of the plant exosomes isolated from the pineapple plant, 1 ng-10 μg of the plant exosomes isolated from the garlic plant, and 1 ng-1 mg of plant exosomes isolated from the pomegranate plant.

4 Claims, 7 Drawing Sheets

(56)                    References Cited

OTHER PUBLICATIONS

Stefania Raimondo, et al., Citrus limon-derived nanovesicles inhibit cancer cell proliferation and suppress CML kenograft growth by inducing TRAIL-mediated cell death, Oncotarget, 2015, pp. 19514-19527, vol. 6, No. 23.

Rudolph D. Paladini, et al., Modulation of Hair Growth with Small Molecule Agonists of the Hedgehog Signaling Pathway, The Journal of Investigative Dermatology, 2005, pp. 638-646, vol. 125, No. 4.

Yizhan Xing, et al., Wnt5a Suppresses β-catenin Signaling during Hair Follicle Regeneration, International Journal of Medical Sciences, 2016, pp. 603-610, vol. 13, No. 8.

Osamu Mori, et al., Effects of Transforming Growth Factor B1 in the Hair Cycle, The Journal of Dermatology, 1996, pp. 89-94, vol. 23.

Jongmin Kim, et al., Isolation of High-Purity Extracellular Vesicles by Extracting Proteins Using Aqueous Two-Phase System, PLOS One, 2015, pp. 1-16.

* cited by examiner

USE OF PLANT EXOSOMES FOR ENHANCING VIABILITY AND HAIR GROWTH CAPACITY OF SKIN CELLS

CROSS REFERENCE TO THE RELATED APPLICATIONS

This application is the national phase entry of International Application No. PCT/TR2020/050796, filed on Sep. 2, 2020, which is based upon and claims priority to Turkish Patent Application No. 2019/13215, filed on Sep. 2, 2019, the entire contents of which are incorporated herein by reference.

TECHNICAL FIELD

The present invention relates to use of plant exosomes as a product having the effect of enhancing viability and, by stimulating the hair follicles, enhancing hair growth in skin cells.

BACKGROUND

Mammalian cells include small vesicular structures called exosomes. When these exosomes are isolated from healthy cells, they can be used to restore the cells, which are damaged or under a certain stress and which cannot complete their self-regeneration, back to their earlier healthy state (Beach, A., Zhang, H. G., Ratajczak, M. Z., & Kakar, S. S. (2014) Exosomes: an overview of biogenesis, composition and role in ovarian cancer. *Journal of ovarian research*, 7(1), 1-11). Recently, use of the stem cells in cell-based therapies is also one of the most promising studies. It is asserted that use of the exosomes released from these cells will have positive effects on wound healing and hair growth/strengthening in clinical application (Levi, S. K., Yeo, M. S. W., Chen, T S., & Lai, R. C. (2011). U.S. patent application Ser. No. 13/879,905).

The vesicles are small sacs which are involved in the transport and storage of substances within the cell and are separated by at least one lipid bilayer from the cytoplasm fluid. Exosomes are vesicles, which are released by many organisms from prokaryotes to high eukaryotes and plants, and which contain lipid bilayer vesicles of different sizes (Ludwig, A. K. and B. Giebel (2012). "Exosomes: small vesicles participating in intercellular communication." Int J Biochem Cell Biol 44(1): 11-15). The importance of these vesicles lies behind the capacity of transferring information to the other cells in order to influence the cell function. Signal transfer via exosomes is carried out by means of biomolecules in many different categories consisting of proteins, lipids, nucleic acid and sugars (Iraci, N., T. Leonardi, F. Gessler, B. Vega and S. Pluchino (2016). "Focus on Extracellular Vesicles: Physiological Role and Signalling Properties of Extracellular Membrane Vesicles." *Int J Mol Sci* 17(2): 171).

Functional interactions of extracellular vesicles with cells were first found in 1982 upon determining experimentally that vesicles isolated from seminal plasma increase sperm motility (Stegmayr, B. and G. Ronquist (1982). "Promotive effect on human sperm progressive motility by prostasomes." *Urol Res* 10(5): 253-257). From this point on, studies have been conducted in many different tissues until today on the developments related to the molecular mechanism of vesicles and bringing the issues left in the dark into light.

Intense hair loss is a problem which can be encountered both in men and women. There are many reasons of this problem depending on hormones, age, stress and mineral deficiency (Norwood, O. T. (1975). Male pattern baldness: classification and incidence. *Southern medical journal*, 68(11), 1359-1365). Although there is no study conducted on cells regarding the viability and hair growth stimulation effects of the plant exosomes related to skin and hair, the characterization of the plant exosomes and their effects on cancer cells have begun to be studied (Raimondo S, Naselli F, Fontana S, et al (2015). *Citrus limon*-derived nanovesicles inhibit cancer cell proliferation and suppress CML xenograft growth by inducing TRAIL-mediated cell death. *Oncotarget.* 6(23):19514-19527).

The European patent application document no. EP3354257, an application in the state of the art, discloses a composition which comprises plant extract-derived extracellular vesicles and is uses for improving skin and preventing hair loss. The said application discloses about the effects of the vesicles obtained by passing the filtered plant juice through different centrifuges. Exosome isolation method involves isolation via ultracentrifuge technique which "is not considered pure" in the literature.

The United States patent application document no. US2018256488, an application in the state of the art, discloses a composition for preventing hair loss and promoting hair growth, containing *ginseng*-derived exosome-like vesicles.

The documents numbered EP2629782A1, WO2017023690A1, WO2017078641A1 and WO2017057881 A1 are also documents known in the art related to use of exosomes in promoting hair growth.

The problems in the applications in the prior art can be listed as follows:

Many substances used as hair growth promoters are chemicals and have toxic effects.

Obtaining the exosomes used as hair growth promoters from animal cells and use thereof are not ethically appropriate.

The side effects resulting due to the fact that the products claiming to promote hair growth and skin rejuvenation are chemicals extend to heart diseases and renal failure.

The high doses used for an effective result are toxic and irritant to the skin.

SUMMARY

The objective of the invention is to enable to revitalize and strengthen unhealthy skin and hair that have lost their vitality, to stop hair loss, to provide faster hair growth by stimulating hair follicles, and to provide a regulating effect in improving the effects such as wrinkles and age spots caused by aging skin cells.

In an embodiment, plant exosomes are used for their effects of enhancing viability, and, by stimulating the hair follicles, enhancing hair growth in skin cells.

In a preferred embodiment, plant exosomes are characterized in that they are isolated from single, double, or triple combinations selected from a group comprising pineapple, garlic, and pomegranate.

In a preferred embodiment, plant exosomes are characterized by a triple combination comprising 1 nanogram-1 milligram of plant exosomes isolated from pineapple plant, 1 nanogram-10 micrograms of plant exosomes isolated from garlic plant, and 1 nanogram-1 milligram of plant exosomes isolated from pomegranate plant.

In a preferred embodiment, plant exosomes are characterized in that they are isolated from the entire plant, fruit, leaf, seed, root, as well as the differentiated tissues of the plant such as the culture medium, stem cell, waste material, shell, or phloem.

In a preferred embodiment, plant exosomes are characterized in that they are isolated by an isolation method selected from a group comprising the isolation methods of two-phase separation, graduated centrifuge, ultrafiltration, chromatographic methods, polymer-based isolation and isolation by microbeads.

In a preferred embodiment, plant exosomes are characterized in that they are isolated by the two-phase liquid system isolation method.

In a preferred embodiment, plant exosomes are characterized in that they are mixed into a solution as personal care products.

In a preferred embodiment, a two-phase liquid system is performed for isolation of the plant exosomes according to the embodiment above from plant lysate, and comprises the steps of:

removing the large size particles and impurities resulting from plant disintegration by centrifugation performed between 2,000 g and 10,000 g for 5-20 minutes, filtering to remove the particles sized 220 nanometers and above, and separating the obtained homogeneous exosome-protein mixture.

BRIEF DESCRIPTION OF THE DRAWINGS

"Use of plant exosomes for enhancing viability and hair growth capacity of skin cells" developed to fulfill the objectives of the present invention is illustrated in the accompanying figures, in which.

DETAILED DESCRIPTION OF THE EMBODIMENTS

Figure 1:
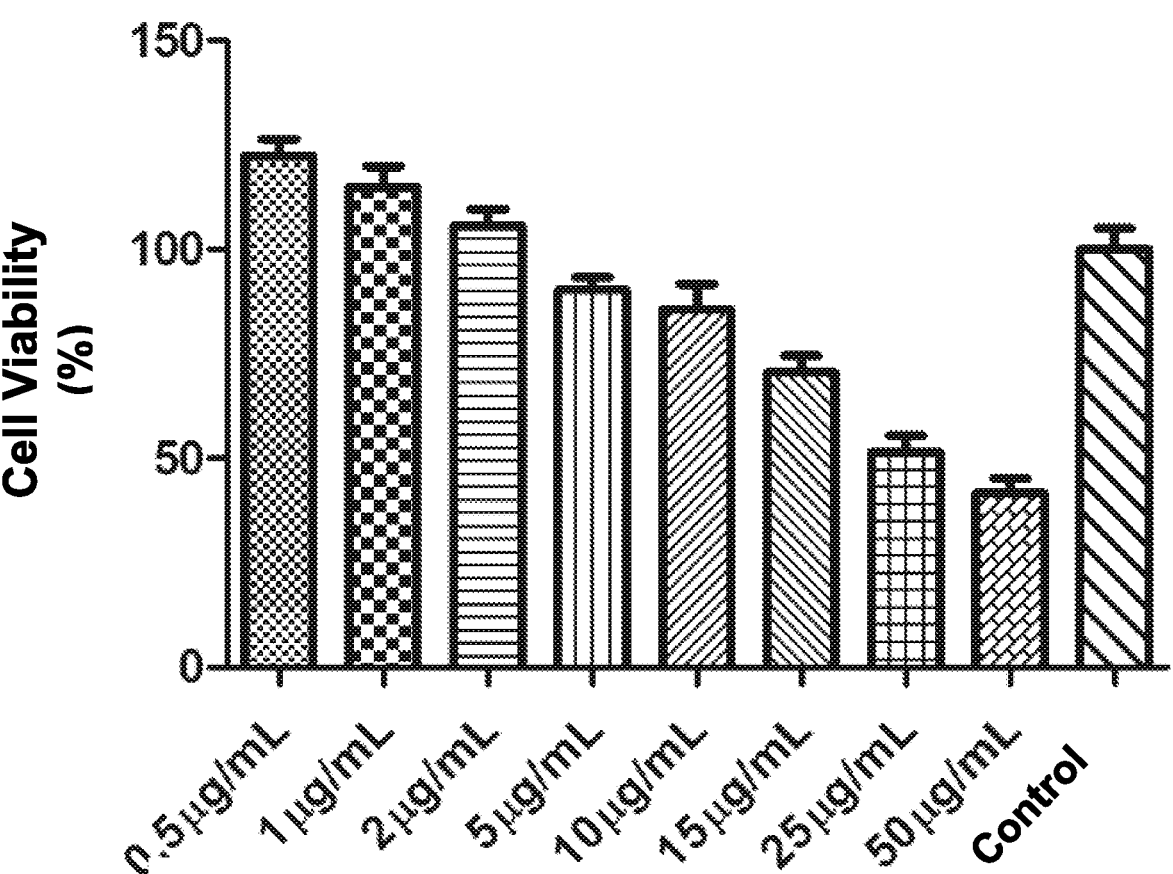
FIG. 1 is a graphical representation of the evaluation of the effect of administration of the exosomes obtained from Garlic to skin cells at different concentrations for 24 hours on cell viability using MTS test.

The present invention relates to use of plant exosomes as a product having the effect of enhancing viability and, by stimulating the hair follicles, enhancing hair growth in skin cells. Pineapple, garlic, and pomegranate are preferred as the plants from which the exosomes are isolated.

Within the scope of the invention, it is aimed to enhance the viability and hair growth capacity of skin cells, and plant-based exosomes are used for this purpose. The effects of the plant exosomes of the present invention can vary according to the plant from which the exosome is isolated. While these can be the entire plant, fruit, leaf, seed, and root, they may also be differentiated tissues like the plant's culture medium, stem cell, waste material, shell, or phloem. The plant exosomes can be isolated by many methods such as isolation by two-phase separation, graduated centrifuge, ultrafiltration, chromatographic methods, polymer-based isolation and isolation by microbeads.

Among the different applications listed above for isolating exosomes from plants, isolation with two-phase liquid system which provides the purest exosome isolation is preferred within the scope of the invention. Within the scope of the invention, the exosomes are isolated from Pineapple, Pomegranate and Garlic. The two-phase liquid system is utilized for isolation of exosomes from plant lysate, which system comprises the steps of removing the large size particles and impurities resulting from plant disintegration by centrifugation performed between 2,000 g and 10,000 g for 5-20 minutes filtering to remove the particles sized 220 nanometers and above, and separating the obtained homogeneous exosome-protein mixture. Exosomes are cleared of nonexosomal proteins, cellular fats and other impurities by utilizing the chemical tendency of the PEG phase to the proteins and of the DEX (dextran) phase to the phospholipid structured membranes in the two-phase liquid system.

Within the scope of the invention, not only the effect of one plant exosome but the use of specific concentrations of 3 plants is discussed. It is observed that the effects of the plant exosomes when used alone are not as high as those when they are used in the combination. In other words, no plant exosome is sufficient for promoting hair growth and skin vitality. Moreover, the scope of the invention involves the effect of not only promoting hair growth, but also the vitality and rejuvenation of skin cells. Accordingly, the scope of the invention involves mixing the plant exosomes into a solution as various personal care products such as creams and shampoos.

The fact that plant exosomes of the present invention have effects of enhancing viability and promoting hair growth on skin and hair cells indicates that they can serve as regulators to revitalize and strengthen unhealthy skin and hair where the skin and hair cells have lost their vitality, to stop hair loss, to provide faster hair growth and to improve the effects such as wrinkles and age spots caused by aging skin cells.

Effective doses of the plant exosomes preferred within the scope of the invention are as follows. Furthermore, as these exosomes can be used in different combinations, a range of use has been determined. These exosomes can be used alone or in combination of 2 or 3. The preferred ratios of composition in a triple combination are as follows:

Pineapple: 1 milligram-1 nanogram

Garlic: 10 milligrams-1 nanogram

Pomegranate 1 milligram-1 nanogram

In addition, it is contemplated and discussed within the scope of the invention that the plant exosomes extracted from these plants can be used with other plant-extracted exosomes.

The advantages of using the plant exosomes of the present invention to enhance the viability and hair growth capacity of skin cells can be listed as follows:

The plant exosome mixture that is used enhances regeneration of the hair follicles in the skin cells.

Enhances viability and regeneration of the skin cells.

Induces hair growth in hair follicles.

Plays a role in eliminating wrinkles on the skin and recuperation of aging skin as it enhances cell viability.

The dose specified in this mixture has a substantial effect in eliminating signs of aging, wrinkles and age spots.

Enables enhancing viability of hair cells and a faster and healthier hair growth by stimulating the hair follicles.

At the same time, the plant exosome mixture enables regrowth of hair as the dormant hair follicle becomes active since the mixture provides an increase in the TGFB1 gene.

The fact that the product is plant-based increases its usability.

Experimental Studies

Figure 2:
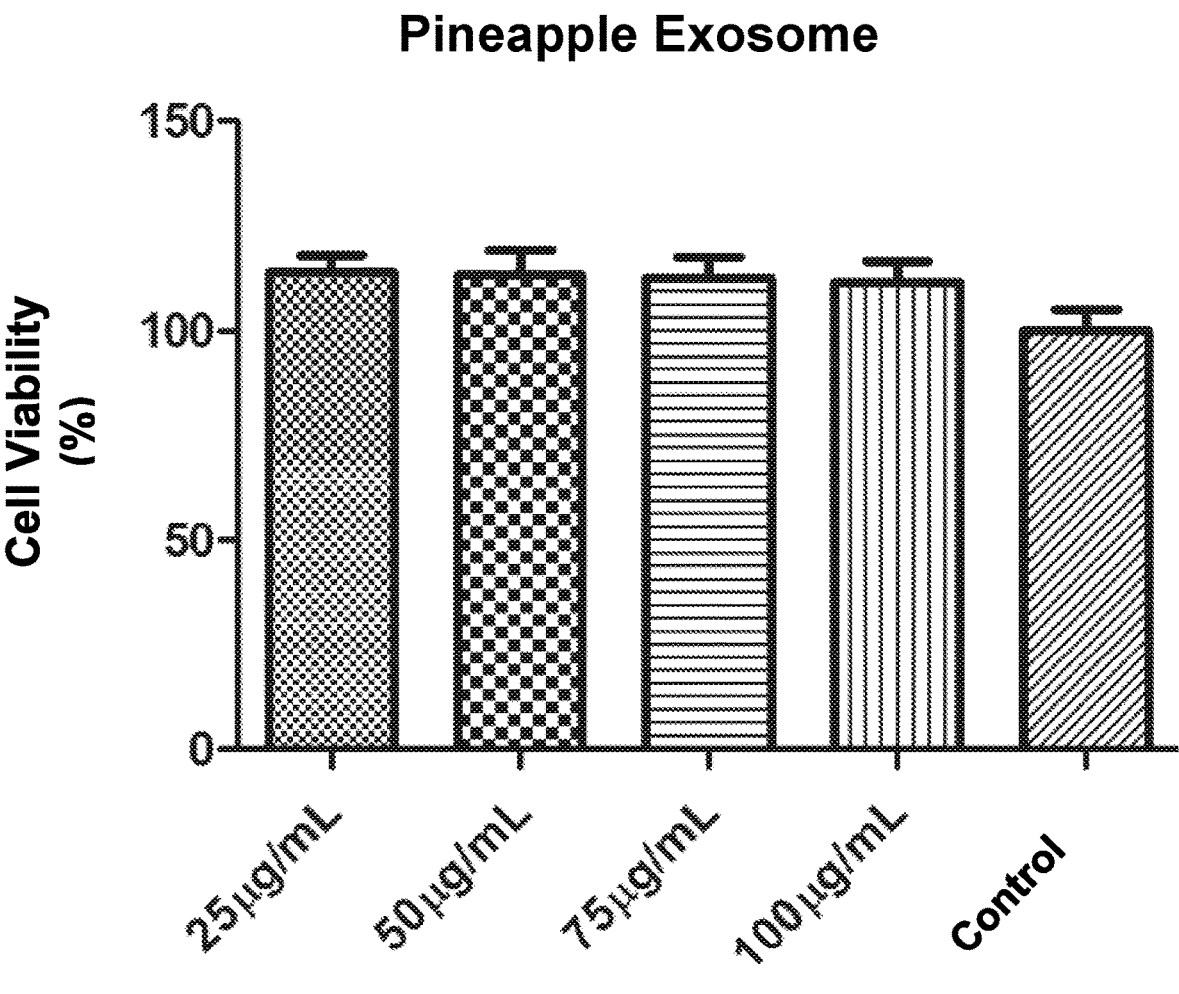
FIG. 2 is a graphical representation of the evaluation of the effect of administration of the exosomes obtained from Pineapple to skin cells at different concentrations for 24 hours on cell viability using MTS test.
Figure 3:
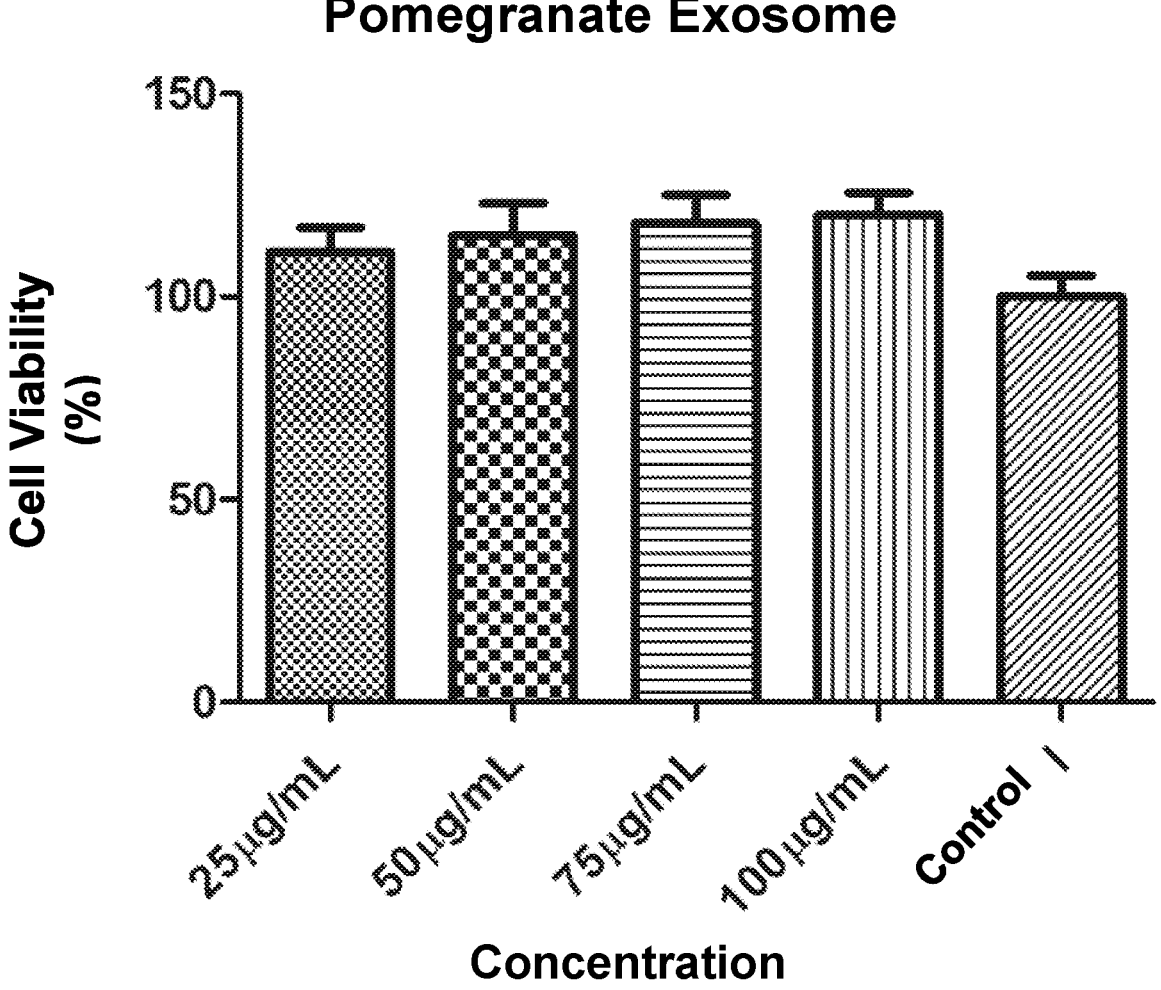
FIG. 3 is a graphical representation of the evaluation of the effect of administration of the exosomes obtained from Pomegranate to skin cells at different concentrations for 24 hours on cell viability using MTS test.
Figure 4:
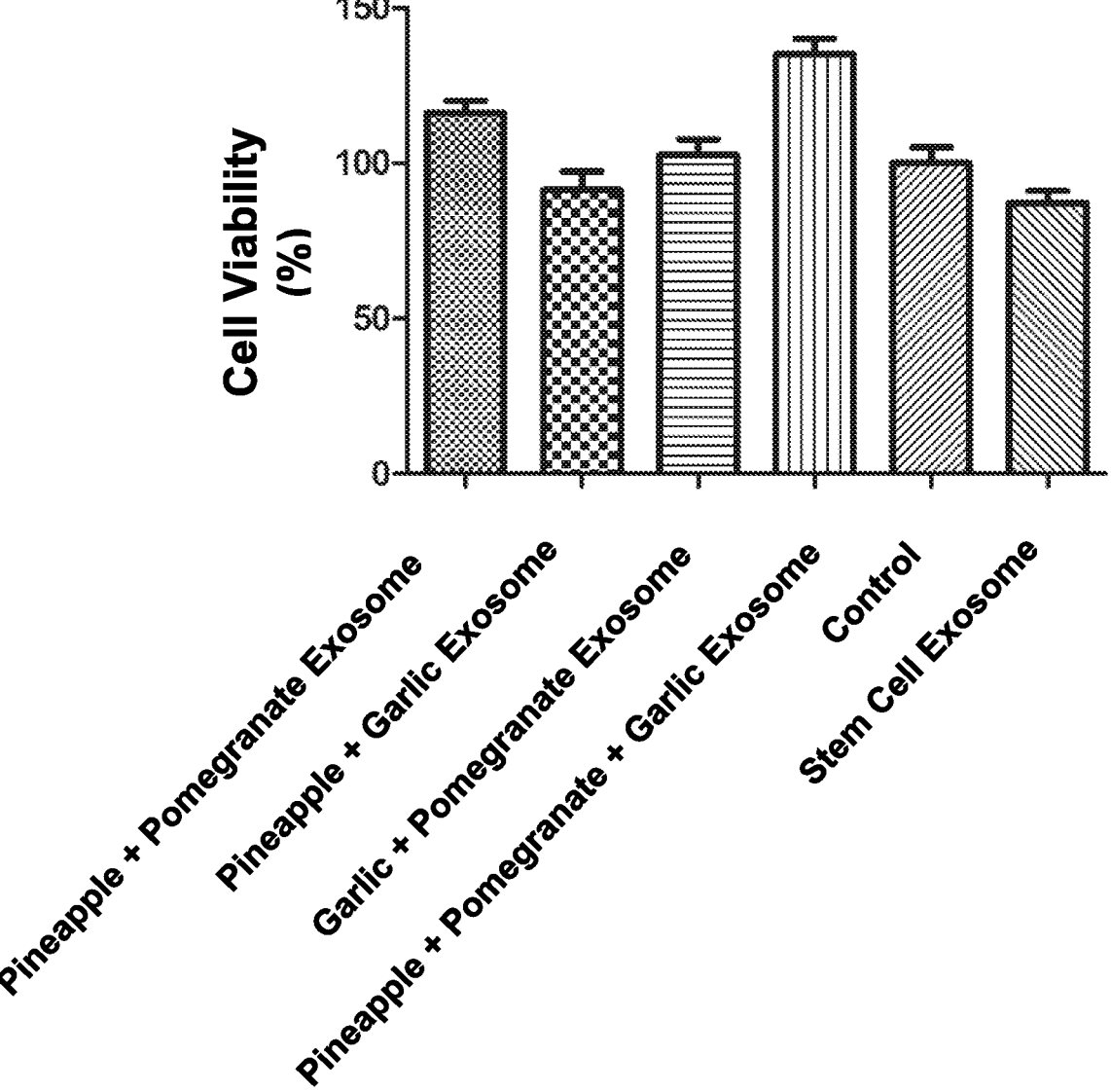
FIG. 4 is a graphical representation of the evaluation of the effect of administration of Garlic-Pineapple-Pomegranate exosomes at non-toxic concentrations for 24 hours on cell viability using MTS test.
Figure 5:
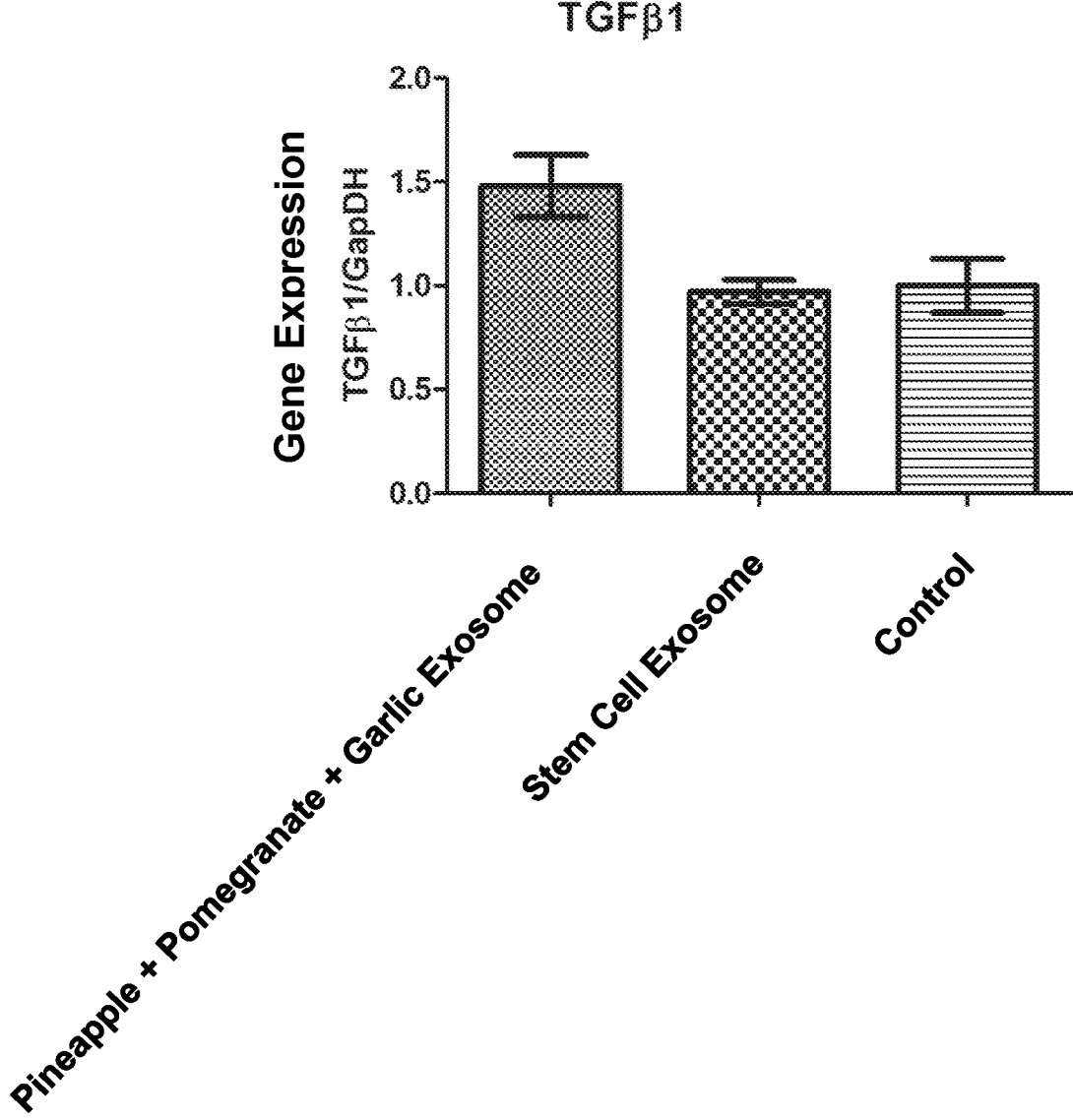
FIG. 5 is a graphical representation of evaluation of administration of the mixtures obtained from plant exosomes and stem cell exosome to skin cells on TGF-B1 gene expression levels.
Figure 6:
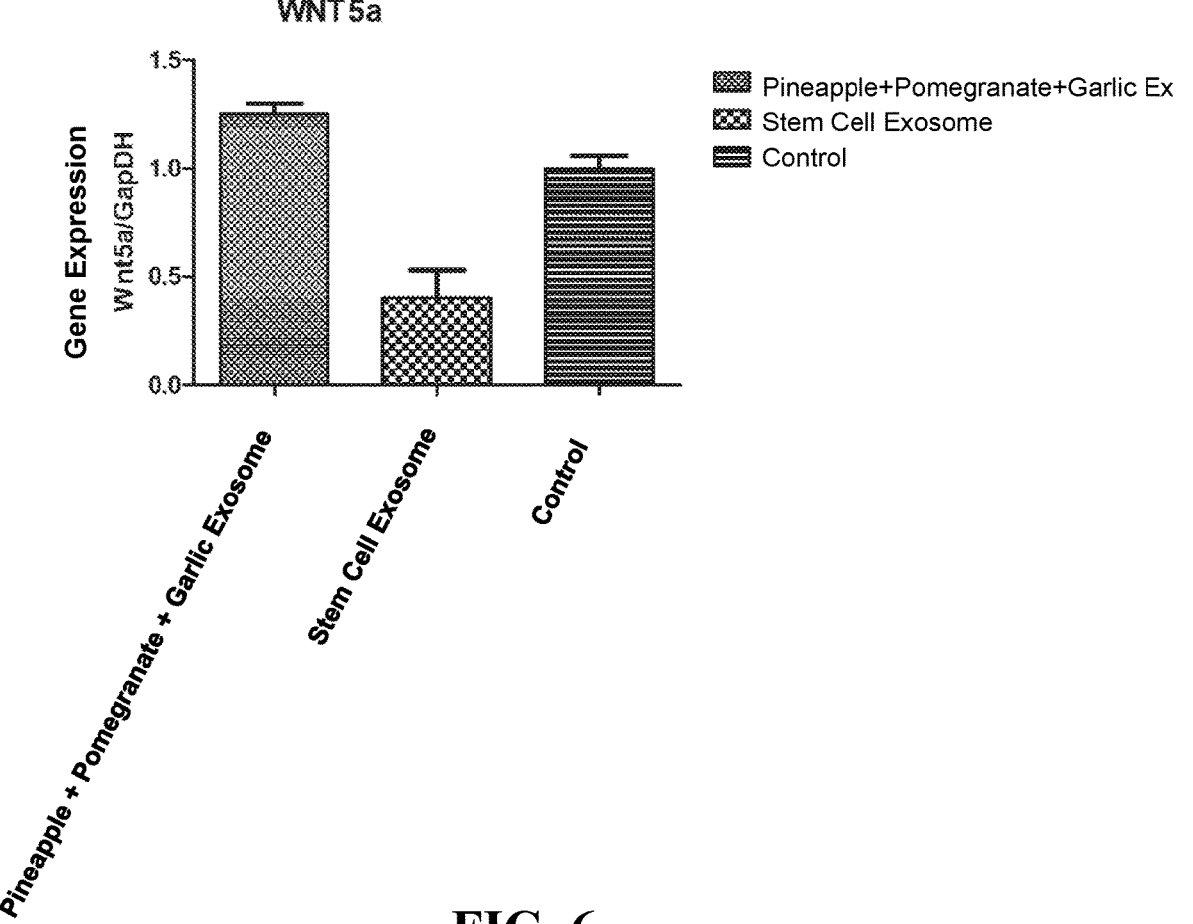
FIG. 6 is a graphical representation of evaluation of administration of the mixtures obtained from plant exosomes and stem cell exosome to skin cells on WNT5a gene expression levels.
Figure 7:
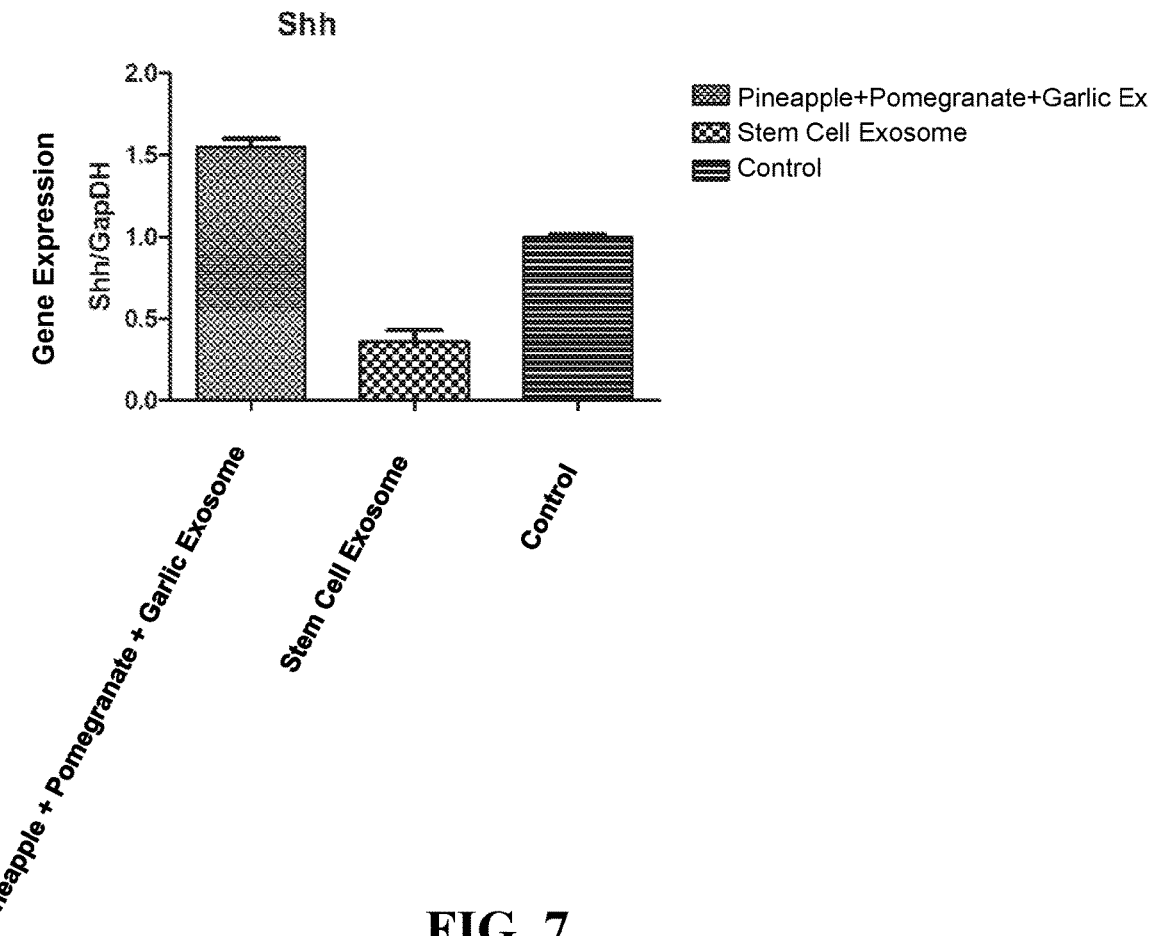
FIG. 7 is a graphical representation of evaluation of administration of the mixtures obtained from plant exosomes and stem cell exosome to skin cells on Shh gene expression levels.

A two-phase fluid system is preferred to be used for separating the homogeneous exosome-protein mixture obtained as a result of the preparation steps. Exosomes are cleared of nonexosomal proteins, cellular fats and other impurities by utilizing the chemical tendency of the PEG phase to the proteins and the DEX phase to the phospholipid structured membranes in the two-phase liquid system. The DEX phase formed by means of the concentrations of the polymers that are used in the solution separate the exosomes. The isolated exosomes were marked by the surface markers CD9, CD63 and HSP70 antibodies which are carried by the exosomes and the exosomes carrying these markers were measured by flow cytometry device. At the same time, the dimensions of the isolated exosomes were measured by means of Zeta Sizer device, and the results are as seen in FIGS. 1-3.

A toxicity analysis was performed to determine the effects of the plant exosomes on viability of skin cells. After the cells were seeded in 96-well culture plates (Corning Glasswork, Corning, NY) at 5000 cells/well in Dulbecco's modified Eagle's medium (DMEM) containing 10% exosome-depleted fetal bovine serum (Invitrogen) and 1% PSA (Biological Industries, Beit Haemek, Israel) in the culture medium, the viability levels of the cells were measured on day 1, 2 and 3. Cell viability was measured by using 3-(4,5-di-methyl-thiazol-2-yl)-5-(3-carboxy-methoxy-phenyl)-2-(4-sulfo-phenyl)-2H-tetrazolium (MTS)-method (CellTiter96 AqueousOne Solution; Promega, Southampton, UK). 10 μl MTS solution was added onto the cells within a 100 μl medium and they were incubated at 37° C. in dark for 2 hours. After the incubation process, cell viability was observed by performing absorbance measurement via ELISA plate reader (Biotek, Winooski, VT) device at 490 nm wavelength.

At the same time, expression levels of the genes related to cell viability and hair growth were measured in order to determine the effect of the exosomes on promoting viability and hair-growth. Cultured cells may lose their own properties and acquire new properties. These properties may be both in morphological level and gene expression level. Real Time PCR method was applied to observe the changes in gene expression level. Total RNAs were isolated, and cDNA was synthesized from the cells that were seeded in 6-well culture plates (Corning Glasswork, Corning, NY) at 50,000 cells/well in Dulbecco's modified Eagle's medium (DMEM). The synthesized cDNAs were mixed with primers in Fermentas Maxima SYBR Green mixture product such that the final volume will be 20 μl and the expression levels of the genes were analyzed by using BTO-RAD device.

As can be seen in the figures, the doses of the plant exosomes required to induce hair growth were determined according to the results of toxicity and cell viability tests shown in FIGS. 1-4. In these figures, the doses that enhance skin cell viability at a maximum level are determined. At the same time, in FIGS. 5-8, the effects of the plant exosome application on the expression levels of the genes of sonic hedgehog (Shh) (Paladini, Rudolph D., et al. (2005) "Modulation of hair growth with small molecule agonists of the hedgehog signaling pathway." *Journal of investigative dermatology* 125.4: 638-646) that is used in determining the hair follicle in the skin cell, WNT5a (Xing Y, Ma X, Guo H, Deng F, Yang J, Li Y. (2016) Wnt5a Suppresses β-catenin Signaling during Hair Follicle Regeneration. *International Journal of Medical Sciences*. 13(8):603-610. doi:10.7150/ijms.15571) that increases the regeneration of the hair follicle, and TGFB1 (Mori, Osamu, Hiroshi Hachisuka, and Yoichiro Sasai. (1996) "Effects of transforming growth factor β1 in the hair cycle." *The Journal of Dermatology* 23.2: 89-94) that is responsible for the growth of hair follicles, were examined, and the plant exosome mixture that is used has been shown to be effective on these genes.

What is claimed is:

1. A method of enhancing viability of skin cells and enhancing hair growth by stimulating hair follicles, comprising administering a composition of plant exosomes to skin cells, wherein administering the composition of plant exosomes induces a transforming growth factor beta 1 (TGF-B1) gene expression, a Wnt family member 5A (WNT5a) gene expression, and a Sonic Hedgehog (Shh) gene expression in the skin cells, and the plant exosomes are isolated from a pineapple plant, a garlic plant, and a pomegranate plant, wherein the administered doses per 100 μL are 1 ng-1 mg of the plant exosomes isolated from the pineapple plant, 1 ng-10 mg of the plant exosomes isolated from the garlic plant, and 1 ng-1 mg of the plant exosomes isolated from the pomegranate plant, and wherein the plant exosomes are isolated from a plant lysate by an isolation method, comprising:

removing large size particles and impurities resulting from plant disintegration by centrifugation performed between 2,000 g and 10,000 g for 5-20 minutes, filtering to remove particles sized 220 nanometers and above, and separating an obtained homogeneous exosome-protein mixture by subjecting the mixture to a two-phase liquid system comprising polyethlene glycol (PEG) and dextran (DEX), and collecting the DEX phase to obtain the plant exosomes, wherein the plant exosomes are cleared of nonexosomal proteins, cellular fats, and other impurities.

2. The method according to claim 1, wherein the plant exosomes are isolated from the group consisting of an entire plant, a fruit, a leaf, a seed, a root, and differentiated tissues of a plant, wherein the differentiated tissues of the plant are selected from the group consisting of a culture medium, a stem cell, a waste material, a shell, and a phloem.

3. The method according to claim 1, further comprising mixing the plant exosomes into a solution as personal care products.

4. The method according to claim 2, further comprising mixing the plant exosomes into a solution as personal care products.

* * * * *